United States Patent [19]
Hashimoto et al.

[11] Patent Number: 5,232,841
[45] Date of Patent: Aug. 3, 1993

[54] EXPRESSION VECTORS CONTAINING A *BACILLUS BREVIS* SIGNAL SEQUENCE

[75] Inventors: Tamotsu Hashimoto, Kyoto; Atsushi Tsujimura, Kawagoe; Shigezo Udaka, Nagoya, all of Japan

[73] Assignee: Hoechst Japan Limited, Tokyo, Japan

[21] Appl. No.: 696,551

[22] Filed: May 9, 1991

[30] Foreign Application Priority Data

May 11, 1990 [JP] Japan .................................. 2-122166
Nov. 30, 1990 [JP] Japan .................................. 2-334575

[51] Int. Cl.$^5$ ...................... C12N 15/10; C12N 15/63; C12N 15/75; C12N 15/67
[52] U.S. Cl. .................................. 435/69.8; 435/69.1; 435/252.31; 435/320.1; 435/833; 935/29; 935/41; 935/48; 536/23.4; 536/24.1; 536/23.1

[58] Field of Search .................... 435/69.1, 69.8, 172.1, 435/172.3, 320.1, 252.5, 252.31, 833; 935/29, 48, 74; 536/27

*Primary Examiner*—Robert A. Wax
*Assistant Examiner*—Dian Jacobson
*Attorney, Agent, or Firm*—Finnegan, Henderson, Farabow, Garrett & Dunner

[57] ABSTRACT

Disclosed is a DNA comprising a nucleotide sequence coding for the signal peptide of *Bacillus brevis* substantially represented by the sequence (I):

Met—Phe—Ser—Lys—Thr—Lys—Met—Gly—Met—Leu— (I)
Met—Gly—Thr—Met—Ala—Val—Val—Leu—Ser—Leu—
Gly—Ser—Ile—Gly—Gly—Ala—Met—Ala

9 Claims, 10 Drawing Sheets

```
        EcoRI  SacI
   1    GAATTCGAGCTCGCCCCTTTTTGGAGTGGAGACGGCCAGTCAATCCCCCAGAGCGTGTCA

61    GAGTCGAAGAGAACTGTGCTTTTTCTTTTCCTCCACTATGTTGACATAGTTTTCTACGAT

121    TTTCCCTCAAGTTTTCCTTTTTTCTCAAACGGGAATCTAAAAATACCCATGTACACTTGG

181    TCTTGTAACAAAGAACAAGCACACTACACGAGCATAGACGAAAGGGTTGAGTGTATATGT
           ↑1                                                    MetP
             BsmI                                                   ↑2
 241    TTAGCAAAACAAAAATGGGAATGCTGATGGGAACGATGGCAGTAGTTTTGAGTCTGGGTA
        heSerLysThrLysMetGlyMetLeuMetGlyThrMetAlaValValLeuSerLeuGlyS

301    GCATAGGCGGAGCAATGGCAGCCGATTCAGCAAAACCAACTTCATTGAATAAACCCGTAG
        erIleGlyGlyAlaMetAlaAlaAspSerAlaLysProThrSerLeuAsnLysProValG
                                                      ↑3
 361    AAGTAAAATTCAAAACCGGCAAGATGGGCCACCACGGTGGGGTGGGCTTCAAAGAAAATA
        luValLysPheLysThrGlyLysMetGlyHisHisGlyGlyValGlyPheLysGluAsnL

421    AAGAGCTGCTCTCGCTGTTAAAGCTGGATGCTGACAAGCTGAAAGAAGAGCTTGCGGCAG
        ysGluLeuLeuSerLeuLeuLysLeuAspAlaAspLysLeuLysGluGluLeuAlaAlaG
                                                      PstI
 481    GGAAAACACTCGCAGCGATTGCACAAGCCCAAGGAGTTGACACTGCAGATGTCGTGGCAC
        lyLysThrLeuAlaAlaIleAlaGlnAlaGlnGlyValAspThrAlaAspValValAlaL

541    TTCTGGTTGACCAGCAAGAGGCCAAACTGAAAGGAGCAGTAACAGCAGGCAAGCTGACGC
        euLeuValAspGlnGlnGluAlaLysLeuLysGlyAlaValThrAlaGlyLysLeuThrG

601    AGGAGCAGGCAGATAAGCTGTCTGAAAATCTGAGCGACCGCGTAAAAGAACAGGTAGAAA
        lnGluGlnAlaAspLysLeuSerGluAsnLeuSerAspArgValLysGluGlnValGluA

661    ACTCGAAACCGGATAAAGGCTTCGGCAGAGGAGGCTTCATCGGTGGCTTCGAGAAAAACG
        snSerLysProAspLysGlyPheGlyArgGlyGlyPheIleGlyGlyPheGluLysAsnG

721    AAGAACTGCTGTCTCTCTTGAAGCTGGATGCCGATAAACTCCAAGAAGAACTGAAAGCCG
        luGluLeuLeuSerLeuLeuLysLeuAspAlaAspLysLeuGlnGluGluLeuLysAlaA

781    ACAAATCGCTGGCTACAATCGCAGAGGCTCAAGGCGTATCTGTGGATGATCTGGTGGCTC
        spLysSerLeuAlaThrIleAlaGluAlaGlnGlyValSerValAspAspLeuValAlaL

841    TGTTGGTAAAACAACAAGAAACCAAGCTGAAAGAGGCAGTAGCGGCAGGCAAGCTCACTC
        euLeuValLysGlnGlnGluThrLysLeuLysGluAlaValAlaAlaGlyLysLeuThrG

901    AGGAGCAAGCCGACAAGATGAATGAAAAAGCGAACGAACGAGTAAAAGAAATGGTGCAAA
        lnGluGlnAlaAspLysMetAsnGluLysAlaAsnGluArgValLysGluMetValGlnA

961    ATACGCATCACGGACGTGGACCGGGTAGAGAAATGGGCTTCGAGAAAAACCAAGAACTGT
        snThrHisHisGlyArgGlyProGlyArgGluMetGlyPheGluLysAsnGlnGluLeuL
```

*Fig. 3A*

```
1021  TGTCTCTCTTGAAGCTGGACGCCGATAAGCTCCAAGAAGAGCTGAAAGCGGAGAAATCGC
      euSerLeuLeuLysLeuAspAlaAspLysLeuGlnGluGluLeuLysAlaGluLysSerL

1081  TGGCTACAATCGCAGAGACCCAAGGCGTATCTGTGGATGATCTGGTGGCTTTGTTGGTAA
      euAlaThrIleAlaGluThrGlnGlyValSerValAspAspLeuValAlaLeuLeuValL

1141  AACAACAGGAAACCAAGCTGAAAGAGGCAGTAGCGGCAGGCAAGCTCACTCAGGAGCAAG
      ysGlnGlnGluThrLysLeuLysGluAlaValAlaAlaGlyLysLeuThrGlnGluGlnA

1201  CCGACAAGATGAATGAAAAAGCGAGCGAACGAGTAAAAGAAATGGTGCAAAATACGCATC
      laAspLysMetAsnGluLysAlaSerGluArgValLysGluMetValGlnAsnThrHisH

1261  ATGGACGTGGACCAGGTAAAGGAATGGGTATCGAGAAAAATGAAGAACTGCTGTCCCTCC
      isGlyArgGlyProGlyLysGlyMetGlyIleGluLysAsnGluGluLeuLeuSerLeuL

1321  TCAAGCTGGATGCAGACAAGCTGAAGGAAGAGCAAAAAGCAGGAAAATCGTTGGCGACTA
      euLysLeuAspAlaAspLysLeuLysGluGluGlnLysAlaGlyLysSerLeuAlaThrI

1381  TCGCCAAGGAGCAAGGTGTAGAAGTGGATGATGTTATCAAGCTCTTGGTAGGTCAACACG
      leAlaLysGluGlnGlyValGluValAspAspValIleLysLeuLeuValGlyGlnHisG

1441  AAACCAAGCTAAAAGAAGCAGTTAAGGCAGGCAAGCTCACACAGGAGCAAGCTGACAAGC
      luThrLysLeuLysGluAlaValLysAlaGlyLysLeuThrGlnGluGlnAlaAspLysA

1501  GCAGCGAGGAATTGACTGCGATGGTGCAAAAGATGGTGGATGGCAGCTTTGAAAAAGTCG
      rgSerGluGluLeuThrAlaMetValGlnLysMetValAspGlySerPheGluLysValV

1561  TTTTCCCAAAACATGAAAAAGAGAAAAAAGACCAGAAGGAAACCATGTAGAAAAGTCAGG
      alPheProLysHisGluLysGluLysLysAspGlnLysGluThrMet***

1621  CAGGTGGGAGTTACTCCCATCTGCTTTTCTATTTTCTCGGGATTGGTCGATGTGCGTCGA

1681  TTTGTACATAAAAACCAACGTGCGAATGAGGTGAAAGGACAATCCGCGAATTGACACACA

SphI  HindIII
1741  GCGGGAAAACACGATACATTCAGAGTAACTTATTGAATGAGGTGGCATGCAAGCTT
```

*Fig. 3 B*

```
                10        20        30        40        50        60
         Ncol
         CCATGGCAACAACATCAACAGGAAATTCGGCACGATTTGTGAACCAGCACCTGTGCGGCT
          MetAlaThrThrSerThrGlyAsnSerAlaArgPheValAsnGlnHisLeuCysGlySer 70        80        90       100       110       120
         CCCACCTAGTGGAAGCTCTCTACCTGGTGTGCGGGGAGCGAGGCTTCTTCTACACACCCA
          HisLeuValGluAlaLeuTyrLeuValCysGlyGluArgGlyPhePheTyrThrProLys 130       140       150       160       170       180
         AGACCCGCCGGGAGGCAGAGGACCCTCAGGTGGGGCAGGTGGAGCTGGGCGGGGCCCTG
          ThrArgArgGluAlaGluAspProGlnValGlyGlnValGluLeuGlyGlyProGly 190       200       210       220       230       240
         GCGCAGGCAGCCTGCAGCCCTTGGCGCTGGAGGGGTCCCTGCAGAAGCGCGGCATCGTGG
          AlaGlySerLeuGlnProLeuAlaLeuGluGlySerLeuGlnLysArgGlyIleValGlu 250       260       270       280       290       300
                                                                  SalI
         AGCAGTGCTGCACCAGCATCTGCTCCCTCTACCAGCTGGAGAACTACTGCAACTAATAGT
          GlnCysCysThrSerIleCysSerLeuTyrGlnLeuGluAsnTyrCysAsn***

CGAC
```

*Fig. 9*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 28 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Met Phe Ser Lys Thr Lys Met Gly Met Leu Met Gly Thr Met Ala Val
1               5                   10                  15

Val Leu Ser Leu Gly Ser Ile Gly Gly Ala Met Ala
                20              25

( 2 ) INFORMATION FOR SEQ ID NO:2:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Ala Lys Pro Thr Ser Leu Asn Lys Pro Val Glu Val Lys Phe Lys Thr
1               5                   10                  15
Gly ( 2 ) INFORMATION FOR SEQ ID NO:3:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:3:

ATGTTTAGCA AAACAAAAAT GGGAATGCTG ATGGGAACGA TGGCAGTAGT TTTGAGTCTG 60
GGTAGCATAG GCGGAGCMAT GGCR 84

( 2 ) INFORMATION FOR SEQ ID NO:4:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:4:

TACGATTTTC CCTCAAGTTT TCCTTTTTC TCAAACGGGA ATCTAAAAAT ACCCATGTAC 60
ACTTGGTCTT 70

( 2 ) INFORMATION FOR SEQ ID NO:5:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:5:

TAACAAAGAA CAAGCACACT ACACGAGCAT AGACGAAAGG GTTGAGTGTA T 51

( 2 ) INFORMATION FOR SEQ ID NO:6:

( i ) SEQUENCE CHARACTERISTICS:
        ( A ) LENGTH: 50 bases
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GCTAAACCAA CTTCTCTGAA CAAACCAGTT GAAGTAAAT TCAAAACTGG 50

( 2 ) INFORMATION FOR SEQ ID NO:7:

( i ) SEQUENCE CHARACTERISTICS:
        ( A ) LENGTH: 77 bases pairs
        ( B ) TYPE: nucleic acid
        ( C ) STRANDEDNESS: both
        ( D ) TOPOLOGY: linear ( i i ) MOLECULE TYPE: DNA (genomic)

-continued ( x i ) SEQUENCE DESCRIPTION: SEQ ID NO:7:

GATGGGAACG ATGGCAGTAG TTTTGAGTCT GGGTAGCATA GGCGGAGCCA TGGCGGATCC 60
TCTAGAGTCG ACCTGCA 77

( 2 ) INFORMATION FOR SEQ ID NO:8:

( i ) SEQUENCE CHARACTERISTICS:
        ( A ) LENGTH: 77 bases pairs
        ( B ) TYPE: nucleic acid
        ( C ) STRANDEDNESS: both
        ( D ) TOPOLOGY: linear ( i i ) MOLECULE TYPE: DNA (genomic)

( x i ) SEQUENCE DESCRIPTION: SEQ ID NO:8:

CATGGCGGCA AATCTTAATG GGACGCTGAT GCAGTATTTT GAATGGTACA TGCCCAATGA 60
CGGCCAACAT TGGAAGC 77

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Asn Ser Asp Ser Glu Xaa Pro Leu Ser His Asp Gly Tyr Xaa Leu His
1               5                   10                  15

Asp Gly Val Xaa
            20

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Met Ala Thr Thr Ser Thr Gly Asn Ser Ala Arg
1               5                   10

( 2 ) INFORMATION FOR SEQ ID NO:11:

( i ) SEQUENCE CHARACTERISTICS:
        ( A ) LENGTH: 1796 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO:11:

GAATTCGAGC TCGCCCCTTT TTGGAGTGGA GACGGCCAGT CAATCCCCCA GAGCGTGTCA 60
GAGTCGAAGA GAACTGTGCT TTTTCTTTTC CTCCACTATG TTGACATAGT TTTCTACGAT 120
TTTCCCTCAA GTTTTCCTTT TTTCTCAAAC GGGAATCTAA AAATACCCAT GTACACTTGG 180
TCTTGTAACA AAGAACAAGC ACACTACACG AGCATAGACG AAAGGGTTGA GTGTAT ATG 239
                                                                                                                        Met

TTT AGC AAA ACA AAA ATG GGA ATG CTG ATG GGA ACG ATG GCA GTA GTT 287
Phe Ser Lys Thr Lys Met Gly Met Leu Met Gly Thr Met Ala Val Val
    -25              -20                 -15

TTG AGT CTG GGT AGC ATA GGC GGA GCA ATG GCA GCC GAT TCA GCA AAA 335
Leu Ser Leu Gly Ser Ile Gly Gly Ala Met Ala Ala Asp Ser Ala Lys
   -10              -5                  1               5

CCA ACT TCA TTG AAT AAA CCC GTA GAA GTA AAA TTC AAA ACC GGC AAG 383

|  |  |  |  |  |  |  |  |  |  |  |  |  |  |  |  |  |
|---|---|---|---|---|---|---|---|---|---|---|---|---|---|---|---|---|
| Pro | Thr | Ser | Leu | Asn<br>10 | Lys | Pro | Val | Glu | Val<br>15 | Lys | Phe | Lys | Thr | Gly<br>20 | Lys |  |
| ATG<br>Met | GGC<br>Gly | CAC<br>His | CAC<br>His<br>25 | GGT<br>Gly | GGG<br>Gly | GTG<br>Val | GGC<br>Gly | TTC<br>Phe<br>30 | AAA<br>Lys | GAA<br>Glu | AAT<br>Asn | AAA<br>Lys | GAG<br>Glu<br>35 | CTG<br>Leu | CTC<br>Leu | 431 |
| TCG<br>Ser | CTG<br>Leu | TTA<br>Leu<br>40 | AAG<br>Lys | CTG<br>Leu | GAT<br>Asp | GCT<br>Ala | GAC<br>Asp<br>45 | AAG<br>Lys | CTG<br>Leu | AAA<br>Lys | GAA<br>Glu | GAG<br>Glu<br>50 | CTT<br>Leu | GCG<br>Ala | GCA<br>Ala | 479 |
| GGG<br>Gly | AAA<br>Lys<br>55 | ACA<br>Thr | CTC<br>Leu | GCA<br>Ala | GCG<br>Ala | ATT<br>Ile<br>60 | GCA<br>Ala | CAA<br>Gln | GCC<br>Ala | CAA<br>Gln | GGA<br>Gly<br>65 | GTT<br>Val | GAC<br>Asp | ACT<br>Thr | GCA<br>Ala | 527 |
| GAT<br>Asp<br>70 | GTC<br>Val | GTG<br>Val | GCA<br>Ala | CTT<br>Leu | CTG<br>Leu<br>75 | GTT<br>Val | GAC<br>Asp | CAG<br>Gln | CAA<br>Gln | GAG<br>Glu<br>80 | GCC<br>Ala | AAA<br>Lys | CTG<br>Leu | AAA<br>Lys | GGA<br>Gly<br>85 | 575 |
| GCA<br>Ala | GTA<br>Val | ACA<br>Thr | GCA<br>Ala | GGC<br>Gly<br>90 | AAG<br>Lys | CTG<br>Leu | ACG<br>Thr | CAG<br>Gln | GAG<br>Glu<br>95 | CAG<br>Gln | GCA<br>Ala | GAT<br>Asp | AAG<br>Lys | CTG<br>Leu<br>100 | TCT<br>Ser | 623 |
| GAA<br>Glu | AAT<br>Asn | CTG<br>Leu | AGC<br>Ser<br>105 | GAC<br>Asp | CGC<br>Arg | GTA<br>Val | AAA<br>Lys | GAA<br>Glu<br>110 | CAG<br>Gln | GTA<br>Val | GAA<br>Glu | AAC<br>Asn | TCG<br>Ser<br>115 | AAA<br>Lys | CCG<br>Pro | 671 |
| GAT<br>Asp | AAA<br>Lys | GGC<br>Gly<br>120 | TTC<br>Phe | GGC<br>Gly | AGA<br>Arg | GGA<br>Gly | GGC<br>Gly<br>125 | TTC<br>Phe | ATC<br>Ile | GGT<br>Gly | GGC<br>Gly | TTC<br>Phe<br>130 | GAG<br>Glu | AAA<br>Lys | AAC<br>Asn | 719 |
| GAA<br>Glu | GAA<br>Glu<br>135 | CTG<br>Leu | CTG<br>Leu | TCT<br>Ser | CTC<br>Leu | TTG<br>Leu<br>140 | AAG<br>Lys | CTG<br>Leu | GAT<br>Asp | GCC<br>Ala | GAT<br>Asp<br>145 | AAA<br>Lys | CTC<br>Leu | CAA<br>Gln | GAA<br>Glu | 767 |
| GAA<br>Glu | CTG<br>Leu | AAA<br>Lys<br>150 | GCC<br>Ala | GAC<br>Asp | AAA<br>Lys | TCG<br>Ser<br>155 | CTG<br>Leu | GCT<br>Ala | ACA<br>Thr | ATC<br>Ile | GCA<br>Ala<br>160 | GAG<br>Glu | GCT<br>Ala | CAA<br>Gln | GGC<br>Gly<br>165 | 815 |
| GTA<br>Val | TCT<br>Ser | GTG<br>Val | GAT<br>Asp | GAT<br>Asp<br>170 | CTG<br>Leu | GTG<br>Val | GCT<br>Ala | CTG<br>Leu | TTG<br>Leu<br>175 | GTA<br>Val | AAA<br>Lys | CAA<br>Gln | CAA<br>Gln | GAA<br>Glu<br>180 | ACC<br>Thr | 863 |
| AAG<br>Lys | CTG<br>Leu | AAA<br>Lys | GAG<br>Glu<br>185 | GCA<br>Ala | GTA<br>Val | GCG<br>Ala | GCA<br>Ala | GGC<br>Gly<br>190 | AAG<br>Lys | CTC<br>Leu | ACT<br>Thr | CAG<br>Gln | GAG<br>Glu<br>195 | CAA<br>Gln | GCC<br>Ala | 911 |
| GAC<br>Asp | AAG<br>Lys | ATG<br>Met<br>200 | AAT<br>Asn | GAA<br>Glu | AAA<br>Lys | GCG<br>Ala | AAC<br>Asn<br>205 | GAA<br>Glu | CGA<br>Arg | GTA<br>Val | AAA<br>Lys | GAA<br>Glu<br>210 | ATG<br>Met | GTG<br>Val | CAA<br>Gln | 959 |
| AAT<br>Asn | ACG<br>Thr<br>215 | CAT<br>His | CAC<br>His | GGA<br>Gly | CGT<br>Arg | GGA<br>Gly<br>220 | CCG<br>Pro | GGT<br>Gly | AGA<br>Arg | GAA<br>Glu | ATG<br>Met<br>225 | GGC<br>Gly | TTC<br>Phe | GAG<br>Glu | AAA<br>Lys | 1007 |
| AAC<br>Asn<br>230 | CAA<br>Gln | GAA<br>Glu | CTG<br>Leu | TTG<br>Leu | TCT<br>Ser<br>235 | CTC<br>Leu | TTG<br>Leu | AAG<br>Lys | CTG<br>Leu | GAC<br>Asp<br>240 | GCC<br>Ala | GAT<br>Asp | AAG<br>Lys | CTC<br>Leu | CAA<br>Gln<br>245 | 1055 |
| GAA<br>Glu | GAG<br>Glu | CTG<br>Leu | AAA<br>Lys | GCG<br>Ala<br>250 | GAG<br>Glu | AAA<br>Lys | TCG<br>Ser | CTG<br>Leu | GCT<br>Ala<br>255 | ACA<br>Thr | ATC<br>Ile | GCA<br>Ala | GAG<br>Glu | ACC<br>Thr<br>260 | CAA<br>Gln | 1103 |
| GGC<br>Gly | GTA<br>Val | TCT<br>Ser | GTG<br>Val<br>265 | GAT<br>Asp | GAT<br>Asp | CTG<br>Leu | GTG<br>Val | GCT<br>Ala<br>270 | TTG<br>Leu | TTG<br>Leu | GTA<br>Val | AAA<br>Lys | CAA<br>Gln<br>275 | CAG<br>Gln | GAA<br>Glu | 1151 |
| ACC<br>Thr | AAG<br>Lys | CTG<br>Leu<br>280 | AAA<br>Lys | GAG<br>Glu | GCA<br>Ala | GTA<br>Val | GCG<br>Ala<br>285 | GCA<br>Ala | GGC<br>Gly | AAG<br>Lys | CTC<br>Leu | ACT<br>Thr<br>290 | CAG<br>Gln | GAG<br>Glu | CAA<br>Gln | 1199 |
| GCC<br>Ala | GAC<br>Asp | AAG<br>Lys<br>295 | ATG<br>Met | AAT<br>Asn | GAA<br>Glu | AAA<br>Lys<br>300 | GCG<br>Ala | AGC<br>Ser | GAA<br>Glu | CGA<br>Arg | GTA<br>Val<br>305 | AAA<br>Lys | GAA<br>Glu | ATG<br>Met | GTG<br>Val | 1247 |
| CAA<br>Gln | AAT<br>Asn<br>310 | ACG<br>Thr | CAT<br>His | CAT<br>His | GGA<br>Gly<br>315 | CGT<br>Arg | GGA<br>Gly | CCA<br>Pro | GGT<br>Gly | AAA<br>Lys<br>320 | GGA<br>Gly | ATG<br>Met | GGT<br>Gly | ATC<br>Ile | GAG<br>Glu<br>325 | 1295 |
| AAA<br>Lys | AAT<br>Asn | GAA<br>Glu | GAA<br>Glu | CTG<br>Leu<br>330 | CTG<br>Leu | TCC<br>Ser | CTC<br>Leu | CTC<br>Leu | AAG<br>Lys<br>335 | CTG<br>Leu | GAT<br>Asp | GCA<br>Ala | GAC<br>Asp | AAG<br>Lys<br>340 | CTG<br>Leu | 1343 |

```
AAG GAA GAG CAA AAA GCA GGA AAA TCG TTG GCG ACT ATC GCC AAG GAG    1391
Lys Glu Glu Gln Lys Ala Gly Lys Ser Leu Ala Thr Ile Ala Lys Glu
            345                 350                 355

CAA GGT GTA GAA GTG GAT GAT GTT ATC AAG CTC TTG GTA GGT CAA CAC    1439
Gln Gly Val Glu Val Asp Asp Val Ile Lys Leu Leu Val Gly Gln His
        360                 365                 370

GAA ACC AAG CTA AAA GAA GCA GTT AAG GCA GGC AAG CTC ACA CAG GAG    1487
Glu Thr Lys Leu Lys Glu Ala Val Lys Ala Gly Lys Leu Thr Gln Glu
        375                 380                 385

CAA GCT GAC AAG CGC AGC GAG GAA TTG ACT GCG ATG GTG CAA AAG ATG    1535
Gln Ala Asp Lys Arg Ser Glu Glu Leu Thr Ala Met Val Gln Lys Met
390                 395                 400                 405

GTG GAT GGC AGC TTT GAA AAA GTC GTT TTC CCA AAA CAT GAA AAA GAG    1583
Val Asp Gly Ser Phe Glu Lys Val Val Phe Pro Lys His Glu Lys Glu
                410                 415                 420

AAA AAA GAC CAG AAG GAA ACC ATG TAG AAAAGTCAGG CAGGTGGGAG          1630
Lys Lys Asp Gln Lys Glu Thr Met
            425                 430

TTACTCCCAT CTGCTTTTCT ATTTTCTCGG GATTGGTCGA TGTGCGTCGA TTTGTACATA  1690
AAAACCAACG TGCGAATGAG GTGAAAGGAC AATCCGCGAA TTGACACACA GCGGGAAAAC  1750
ACGATACATT CAGAGTAACT TATTGAATGA GGTGGCATGC AAGCTT                 1796
```

( 2 ) INFORMATION FOR SEQ ID NO:12:

( i ) SEQUENCE CHARACTERISTICS:
        ( A ) LENGTH: 304 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQUENCE ID NO:12:

```
CC ATG GCA ACA ACA TCA ACA GGA AAT TCG GCA CGA TTT GTG AAC CAG    47
   Met Ala Thr Thr Ser Thr Gly Asn Ser Ala Arg Phe Val Asn Gln
   -10                 -5                          1

CAC CTG TGC GGC TCC CAC CTA GTG GAA GCT CTC TAC CTG GTG TGC GGG   95
His Leu Cys Gly Ser His Leu Val Glu Ala Leu Tyr Leu Val Cys Gly
  5               10                  15                  20

GAG CGA GGC TTC TTC TAC ACA CCC AAG ACC CGC CGG GAG GCA GAG GAC   143
Glu Arg Gly Phe Phe Tyr Thr Pro Lys Thr Arg Arg Glu Ala Glu Asp
                25                  30                  35

CCT CAG GTG GGG CAG GTG GAG CTG GGC GGG GGC CCT GGC GCA GGC AGC   191
Pro Gln Val Gly Gln Val Glu Leu Gly Gly Gly Pro Gly Ala Gly Ser
            40                  45                  50

CTG CAG CCC TTG GCG CTG GAG GGG TCC CTG CAG AAG CGC GGC ATC GTG   239
Leu Gln Pro Leu Ala Leu Glu Gly Ser Leu Gln Lys Arg Gly Ile Val
        55                  60                  65

GAG CAG TGC TGC ACC AGC ATC TGC TCC CTC TAC CAG CTG GAG AAC TAC   287
Glu Gln Cys Cys Thr Ser Ile Cys Ser Leu Tyr Gln Leu Glu Asn Tyr
    70                  75                  80

TGC AAC TAA TAGTCGAC                                              304
Cys Asn
85
```

EXPRESSION VECTORS CONTAINING A *BACILLUS BREVIS* SIGNAL SEQUENCE

BACKGROUND OF THE INVENTION

1. Field of the Art

The present invention relates to a DNA sequence coding for a so-called signal peptide and to its use for producing proteins by means of genetic engineering. More particularly, the present invention relates to a process for producing proteins with us of *Bacillus brevis* as a host and also to a DNA sequence required therefor.

2. Related Art

A method for producing heterologous proteins in microorganisms with use of recombinant DNA techniques has been widely used for the production of medical and pharmaceutical products.

It is *Escherichia coli* that has been most popularly used as a host microorganism for such a method. However, the heterologous protein produced is usually retained within cells of *E. coli* as the host. Thus, it is required for the purification of the heterologous protein to destroy the cells and to remove a number of compounds such as proteins derived from *E. coli* or the like. Furthermore, the heterologous proteins which are produced in abundance in the limited space of the cells sometimes form inclusion bodies, so that great efforts are often required to regenerate activities of the heterologous proteins.

On the other hand, in a system in which *Bacillus subtilis*, yeasts or the like are used as host microorganisms, there is an advantage that heterologous proteins produced are generally secreted extracellularly from the host cells and thus the products are easily recovered. Such an advantage in *Bacillus subtilis* or the like as the host presumably depends on a mechanism that the host microorganism has a gene carrying specific genetic informations and produces a desired protein as a precursor in which peptide chains, so-called signal peptides, are bound, and the precursor is passed through the cell membrane and secreted extracellularly or into the periplasm, whereupon the signal peptide chains are cleaved off and mature proteins are obtained.

As an example of a system in which a microorganism of genus Bacillus is used, there has bee reported a successful example of the secretion of a large amount of foreign genetic products into a culture medium by using *Bacillus brevis* 47 which secretes a protein in an amount as much as 12 g/l into the medium under the optimal culture condition [S. Udaka, (1976) Agric. Biol. Chem., 40, 523–528; S. Miyashiro, H. Enei, K. Tekeinami, Y. Hirose, T. Tsuchida and S. Udaka (1980), Agric. Biol. Chem., 44, 2297–2303], linking a promotor of a gene coding for MWP which is one of the proteins secreted by the microorganism and a DNA coding for a signal peptide with a foreign gene such as human epidermal growth factor or the like and introducing the linked DNA into the *Bacillus brevis* 47 [H. Yamagata, et al., (1989), Proc. Natl. Acad. Sci. U.S.A., 86, 3589–3593].

However, the foreign genetic products thus produced may possibly be decomposed in a culture medium because of the proteolytic enzymes extracellularly secreted in a small amount by the *Bacillus brevis* 47.

SUMMARY OF THE INVENTION

The object of the present invention is to solve the above described problems by the use of an expression system constructed by us in which use is made of the regulation site of a gene coding for a protein BBRP42 which has now been discovered and found to be secreted at the initial stage of culture where proteolytic enzymes have not been secreted too much.

Thus, the present invention relates to a DNA coding for a signal peptide and comprises a DNA sequence coding for the signal peptide substantially represented by the following amino acid sequence (I). (Seq. ID No 1):

Met—Phe—Ser—Lys—Thr—Lys—Met—Gly—Met—Leu— (I)
Met—Gly—Thr—Met—Ala—Val—Val—Leu—Ser—Leu—
Gly—Ser—Ile—Gly—Gly—Ala—Met—Ala

The present invention also relates to an expression vector, which comprises the aforementioned DNA coding for the signal peptide and a DNA coding for a desired heterologous protein linked at the downstream end of the former DNA as well as a DNA required for the expression of these foreign genes.

Furthermore, the present invention relates to a process for producing a desired protein, which comprises transforming a host cell with the vector according to the present invention, and culturing the transformant formed in a culture medium to produce the protein secreted in the culture medium.

The ligation and expression of the DNA coding for the signal peptide according to the present invention and the DNA coding for a desired heterologous protein successfully lead to the extracellular secretion and production of the desired heterologous protein from the host cell.

Particularly, when a strain of genus Bacillus is used as a host, a desired heterologous protein is produced in a culture medium prior to the secretion of a proteolytic enzyme derived from genus Bacillus, so that homogeneous protein can be produced in a high yield.

BRIEF DESCRIPTION OF THE DRAWINGS

FIGS. 3A–3B shows a DNA sequence from the EcoRI site to the HindIII site of pBRE-1 which is one of the deletion mutants prepared in Example 3, and an amino acid sequence of BBRP42, in which the base pairs at position 1 to 13 and 1791 to 1796 indicate the cloning sites inherent in the vector; and ↑1 represents the transcription initiating point, ↑2 represents the origin of the secretion signal (translation initiating point), and ↑3 represents the origin of BBRP42;

FIG. 9 shows the amino acid sequence of the proinsulin derivative of a monkey and the DNA sequence thereof.

DETAILED DESCRIPTION OF THE INVENTION

Signal peptide

Figure 1:
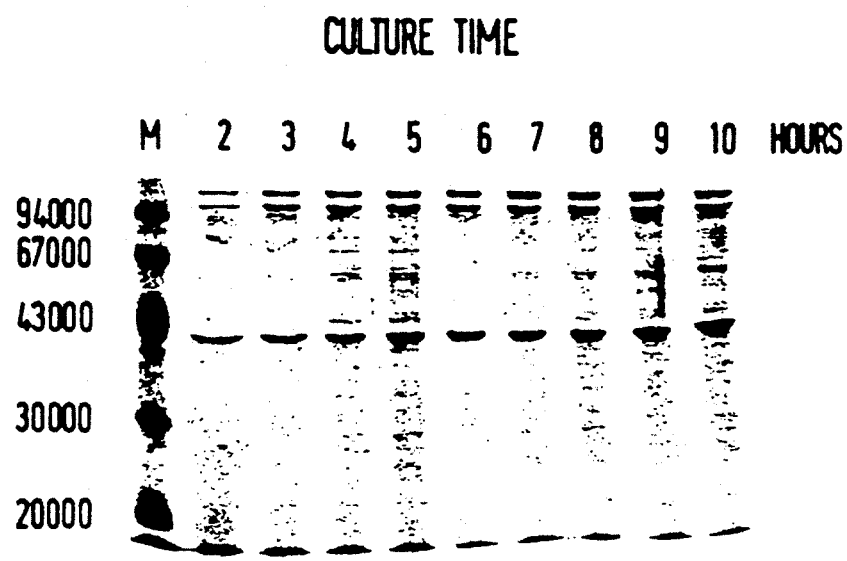
FIG. 1 shows a result of the SDS-polyacrylamide gel electrophoresis of the proteins which have been prepared in Experimental Example 1 and secreted into a culture medium at an initial stage of culture.
Figure 2:
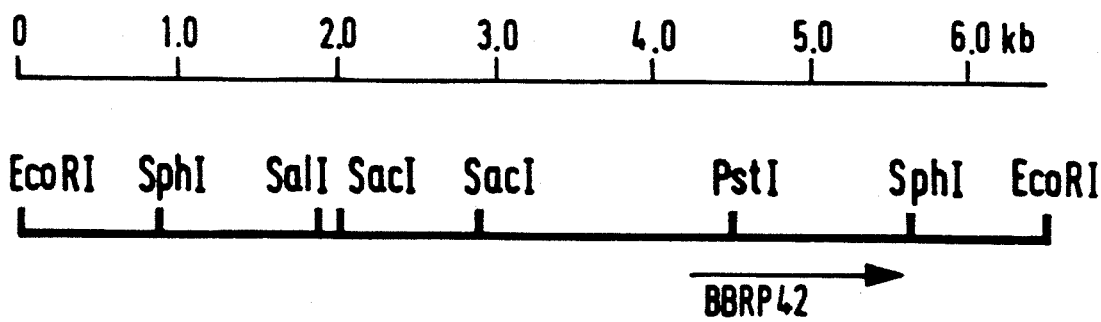
FIG. 2 shows a restriction enzyme cleavage map of a DNA fragment containing a gene coding for BBRP42.
Figure 4:
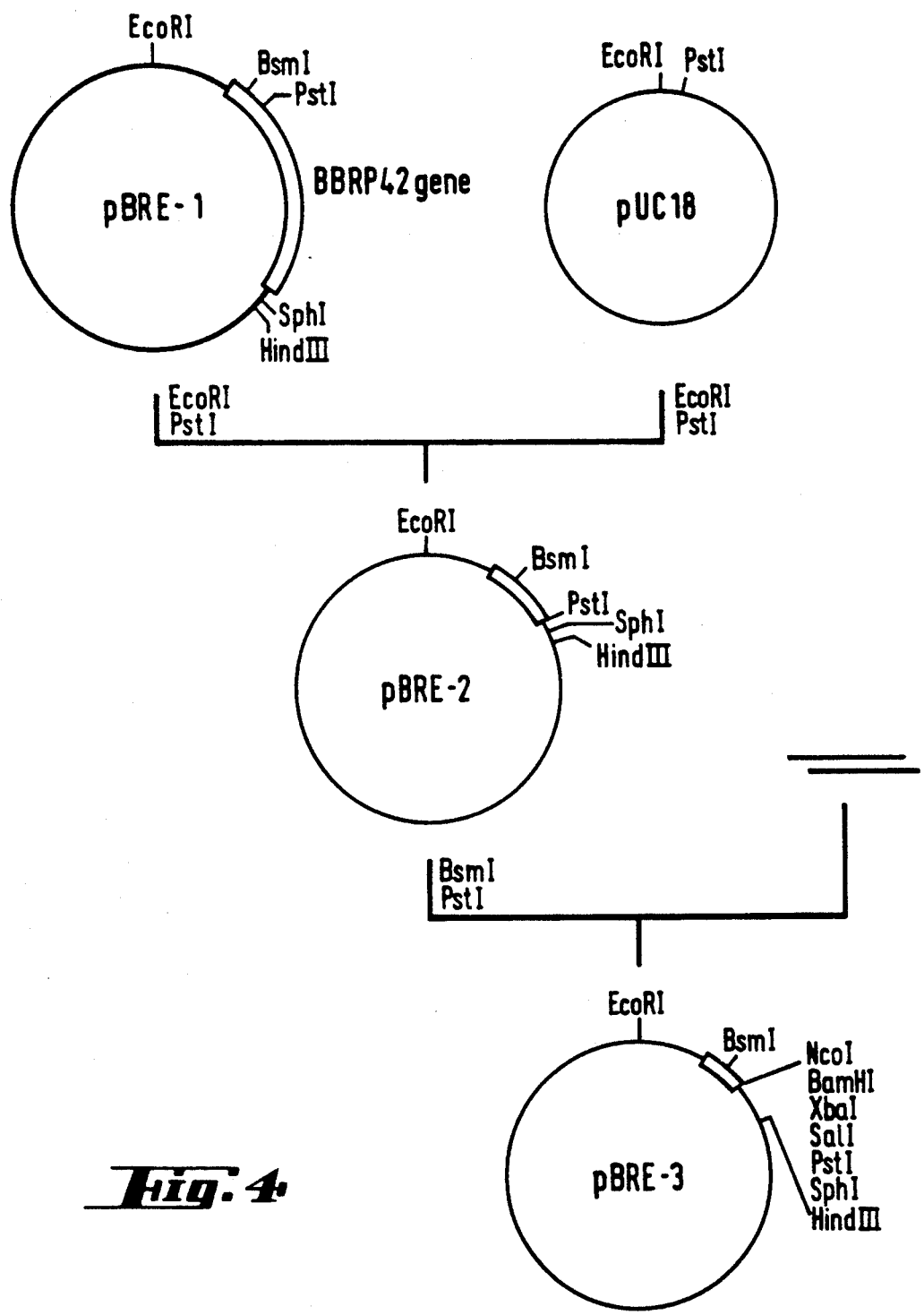
FIG. 4 shows the process for preparing the expression unit vector.
Figure 5:
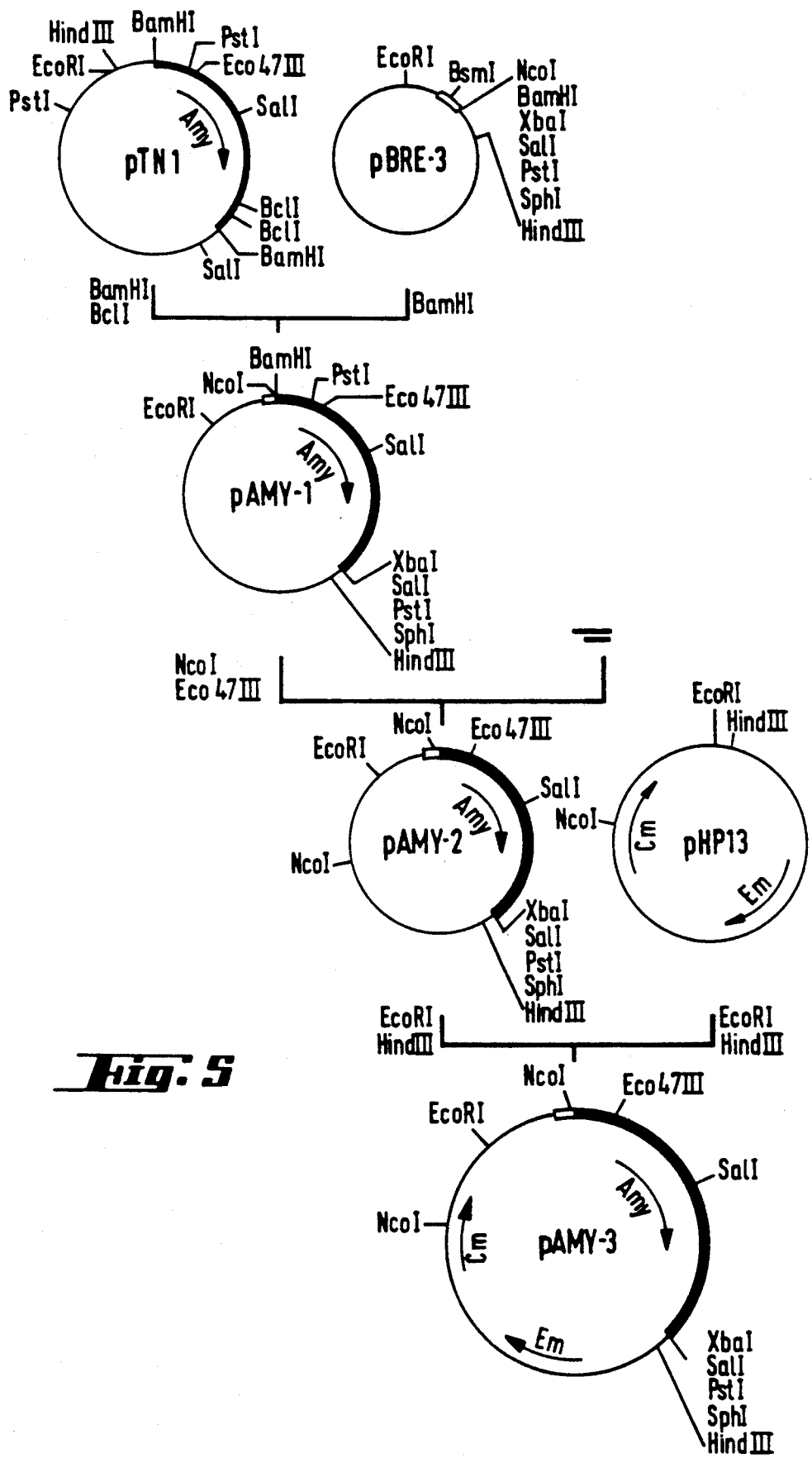
FIG. 5 shows the process for constructing the *B. licheniformis* α-amylase expression vector.
Figure 6:
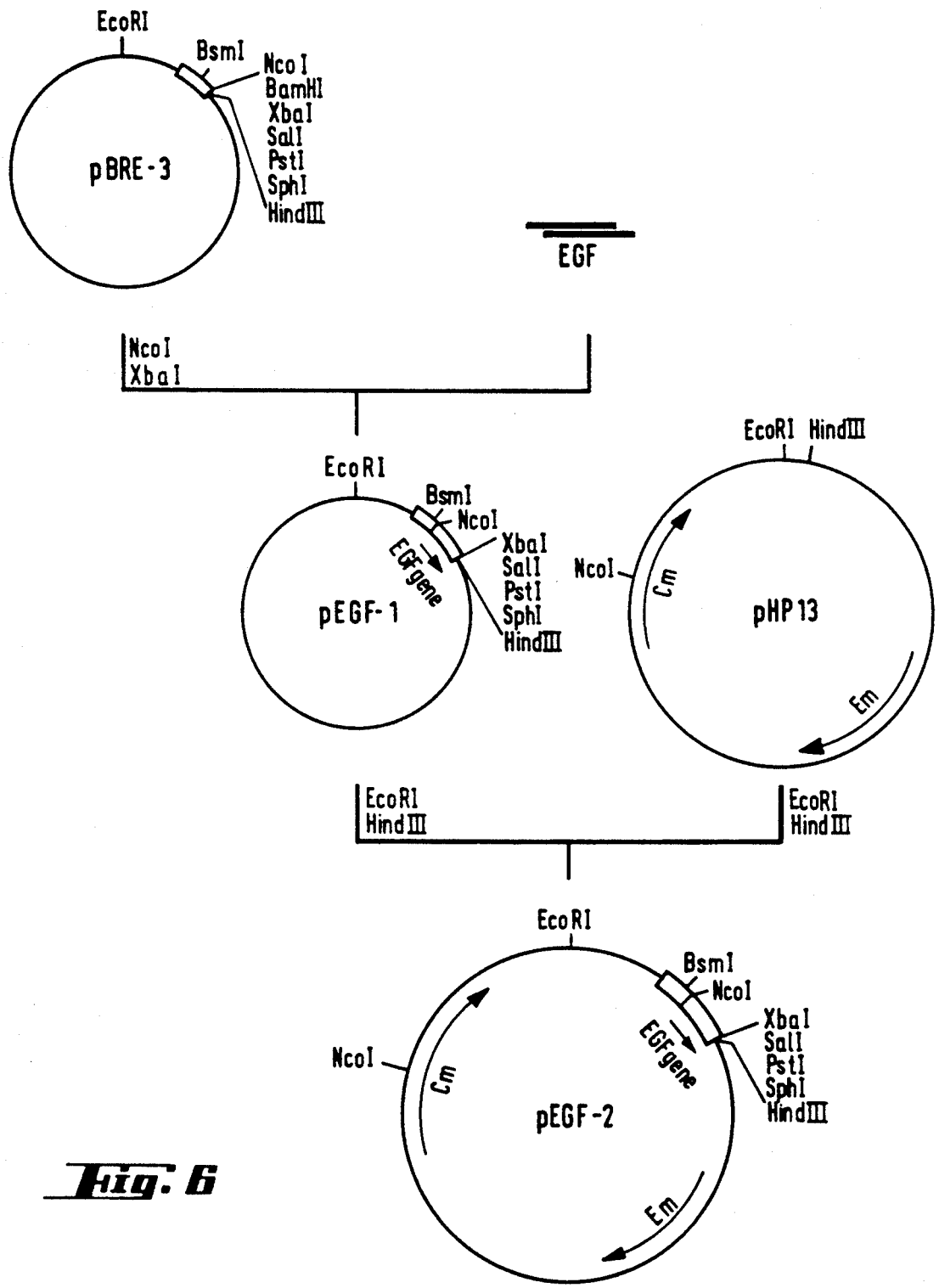
FIG. 6 shows the process for constructing the human epidermal factor expression vector.

The DNA according to the present invention comprises a DNA sequence coding for the signal peptide, which has an amino acid sequence substantially represented by the aforementioned sequence (I).

Thus, the DNA according to the present invention is defined by a peptide comprising an amino acid sequence which is coded for by the DNA. The peptide is the so-called signal peptide which acts in extracellularly secreting an organismic product produced within a cell, and the amino acid sequence is substantially represented by the aforementioned sequence (I). The phraseaology "the amino acid sequence substantially represented by the aforementioned sequence (I)" means that the peptide can have deletion, substitution, addition or the like for from one to three of the amino acids as far as it acts as the so-called signal peptide.

The amino acid sequence represented by the sequence (I) has been accomplished on the basis of the analysis of genes coding for BBRP42 which is a protein secreted into a culture medium at an initial stage of the culture of *Bacillus brevis* 47.

BBRP42 is a novel protein having the following properties:

(1) It has a molecular weight of about 42,000 by SDS-PAGE;

(2) It has the following amino acid sequence corresponding to the positions 4-20 from the N-terminus (Seq. ID No 2):

Ala—Lys—Pro—Thr—Ser—Leu—Asn—Lys—Pro—Val—Glu—

Val—Lys—Phe—Lys—Thr—Gly; and (3) It is secreted into a culture medium at an initial stage earlier than that of MWP which is a protein inherent in *Bacillus brevis* 47.

DNA coding for a signal peptide

The DNA coding for the signal peptide according to the present invention is the one which comprises a DNA sequence coding for the aforementioned sequence (I) and the one which comprises a DNA sequence corresponding to the change of the amino acid sequence of a peptide acting as the signal peptide described above.

A typical sequence of the DNA according to the present invention is represented by the following sequence (II) (Seq ID No 3):

ATG—TTT—AGC—AAA—ACA—AAA—ATG—GGA—

ATG—CTG—ATG—GGA—ACG—ATG—GCA—GTA—

GTT—TTG—AGT—CTG—GGT—AGC—ATA—GGC—

GGA—GCM—ATG—GCR  (II)

wherein M represents A or C, and R represents A or G.

For an amino acid sequence of a peptide given, the DNA sequence coding for it can be easily specified upon the reference to the so-called code table and a variety of DNA sequences coding for the aforementioned amino acid sequence can be selected appropriately. Thus, the DNA coding for the signal peptide according to the present invention means the one where DNA sequence is the aforementioned sequence or the degenerated isomer thereof. In this connection, the term "degenerated isomer" means the DNA which has the same DNA sequence and codes for the same peptide except that a codon in the degeracy relation is used.

Acquirement of DNA coding for signal peptide

The DNA sequence of the DNA according to the present invention is specified, and thus one possible means for obtaining the DNA is the production of it according to the method for synthesizing nucleic acids.

The DNA according to the present invention can be also prepared by the method for cleaving it out from the gene of *Bacillus brevis*. Specific examples of such methods for obtaining the DNA may include a method in which the DNA derived is obtained from the gene library inherent in the *Bacillus brevis* 47 by means of a method which has been usually used in the field of genetic engineering such as a hybridization method in which an appropriate probe is used. As for the specific examples of such methods, see Experimental Examples described hereinafter.

Use of DNA coding for signal peptide

The DNA according to the present invention is a DNA coding for a signal peptide. Accordingly, a desired protein can be produced extracellularly from a host cell by the transformation of the host cell with a DNA, particularly in the form of an expression vector, which comprises the DNA coding for a signal peptide and a DNA linked to the downstream end of the DNA in such a state that these DNAs can be replicated in the host cell and these genetic informations can be expressed as well.

The DNA according to the present invention is suitable for constructing a vector to be used in a host-vector system in which a microorganism of genus Bacillus is the host and utilizing it in transforming therewith the microorganism of genus Bacillus, particularly *Bacillus brevis*, since the DNA according to the present invention can produce a heterologous protein in a culture medium prior to the secretion of a proteolytic enzyme derived from the bacterium of genus Bacillus into the medium.

Expression vector according to the present invention

Accordingly, the expression vector according to the present invention is characterized in that the DNA coding for the above-mentioned signal peptide and a DNA coding for a desired heterologous protein linked to the downstream end thereof are comprised in it together with a DNA required for the expression of these foreign genes.

Particularly, the expression vector according to the present invention is preferably constructed as an expression vector to be used in a host-vector system in which a microorganism of genus Bacillus is the host because of the above-mentioned reason.

As the procedure or method for constructing the vector according to the present invention, there may be used the procedure or method usually used in the field of molecular biology, biological engineering or genetic engineering.

For example, when the DNA inherent in the aforementioned protein BBRP42 is directly used as the DNA coding for the signal peptide according to the present invention, the vector according to the present invention can be obtained by the following procedure. That is, the vector according to the present invention can be obtained by incorporating and cloning the DNA obtained by the screening of the gene library of the above-mentioned BBRP42 into a vector which can be replicated in a host such as E. coli, and then incorporating the DNA thus obtained in such form that a DNA coding for a desired heterologous protein is linked at the downstream end thereof, in a vector which can be replicated in a predetermined host.

Specific examples of the vectors replicable in microbial cells of genus Bacillus used as a host may include plasmids such as pTA1060, pUB110, pE194, pC194 and the like and DNAs derived from these plasmids.

Furthermore, it is preferred to use, as the vector according to the present invention, a vector which can be replicated in either of a microorganism used for the cloning of the DNA which encodes a signal peptide obtained from a gene library, such as E. coli, and a microorganism used as a host in the production of a protein such as a bacterium of genus Bacillus, i.e. shuttle vector, since the operation of transferring the DNA fragment can be omitted. As the shuttle vector of E. coli and a bacterium of genus Bacillus, it is possible to use plasmids such as pHP13 or the like (P. Haima, S. Bron, G. Venema, Mol. Gen. Genet., 209, 335–342, 1987).

These plasmids are required to contain selection markers such as resistance to chloramphenicol, resistance to erythromycin, resistance to neomycin, resistance to tetracyclin, resistance to streptomycin or the like.

The expression vector according to the present invention is required to have DNAs which are required for the expression of a foreign gene comprising a DNA coding for the signal peptide and a DNA coding for a heterologous protein, i.e. promoter, transcription regulating signals and translation regulating signals such as a transcription initiating signal, a ribosome binding site, a translation terminating signal, a transcription terminating signal and the like to ensure that the vector will, upon introduction into a host cell, secrete and express a desired heterologous protein.

These factors are sometimes contained preliminarily in the original vector, and in this case the regulating factors in the original vector can as such be used. As having been described above, when the DNA which encodes the signal peptide and is obtained from the protein BBRP42 is used directly, it is advantageous to clone not only the DNA coding for the signal peptide but also regulation regions such as the promoter as well.

When a bacterium of genus Bacillus is used as a host, it is particularly preferred to incorporate a promoter for expressing these foreign genes at an initial stage of culture. Specific examples of the preferably promoter may include a promoter which has at least 30 base pairs of the following DNA sequence (III). (Seq. ID No 4):

TACGATTTTCCCTCAAGTTTTCCTTTTTTCTCAAA

CGGGAATCTAAAAATACCCATGTACACTTGGTCTT    (III)

Moreover, it is preferred that a translation regulating signal represented by the following DNA sequence (IV) as a DNA required for the expression of the foreign gene is comprised between the transcription initiating site and translation initiating site. (Seq ID No 5)

GTAACAAAGAACAAGCACACTACACGAGCATAGACG

AAAGGGTTGAGTGTAT    (IV)

The heterologous proteins which can be produced by the present invention are not limited. Typical examples thereof may include, in addition to h-EGF described in the above-mentioned literature in which a foreign protein has been produced with Bacillus brevis 47, interferons, a variety of interleukins, insulin, NGF, TNF, GM-CSF, blood coagulation factor VIII, specific antigenic proteins of various diseases or the like.

Method for preparing the desired protein

The method for preparing the desired protein according to the present invention comprises, as described above, transforming a host cell with the expression vector according to the present invention and culturing the transformant obtained to secrete the desired protein in a culture medium.

As the host microorganism, strains of genus Bacillus are particularly used. As an example of the preferably strains of genus Bacillus, there is mentioned Bacillus brevis. Typical examples of Bacillus brevis include Bacillus brevis 47 (FERM P-7224), 481, 144, 899 and the like.

Transformation may be carried out by the conventional method in the art.

The culture of the transformant thus obtained produces and accumulates the desired foreign protein extracellularly from the host microorganism (that is, in a culture medium).

The culture and culture condition of the transformant are essentially the same as those of the host microorganism used. Also, the desired protein can be recovered from the culture medium and purified according to the usual method.

EXPERIMENTAL EXAMPLE

Example 1

Investigation of proteins in supernatant of culture medium of Bacillus brevis 47 in the initial stage of culture Cells of Bacillus brevis 47 strain were cultured overnight in a Tlura medium (0.3% $K_2HPO_4$, 0.2% $(NH_4)_2SO_4$, 0.025% $MgSO_4 \cdot 7H_2O$, 0.3% peptone, 0.2% meat extract, 2% glucose, 0.2% urea and 0.01% uracil). The resultant medium was diluted 100 times with the same Tlura medium, and shaking culture was carried out at 37° C. while measuring the absorbance at 660 nm. After incubation for 2 to 10 hours, the cells were removed from the culture by centrifugation, ammonium sulfate was added to the supernatant so that it is saturated up to 90%, and then the mixture was left standing at 4° C. After centrifugation, a portion of the suspension of the resultant precipitate in an amount corresponding to 1 ml of the culture fluid having the absorbance of 0.01 was subjected to SDS polyacrylamide gel electrophoresis according to the method of Laemmli (Nature, 1970, 227, 680-685). Staining of the gel with Coomassie Brilliant Blue gave a band corresponding to a protein of a molecular weight of about 42,000 in addition to those of previously reported MWP and OWP (H. Yamada et al., (1982) J. Bacterilogy, 148, 322-332) in the supernatant of the culture medium in the early stage of the culture. This protein was named BBRP42.

Example 2

Purification of BBRP42 and determination of amino acid sequence of N-terminus thereof (1) Purification of BBRP42

The culture medium of the cells of *Bacillus brevis* 47 which had been cultured overnight in the Tlura medium was diluted 100 times with the same Tlura medium as in Example 1, and shaking culture was carried out at 37° C. until the absorbance at 660 nm reached 0.7. The ice-cooled culture medium was added with PMSF (phenylmethanesulfonyl fluoride) to a final concentration of 1 nM and centrifuged to remove the cells. To 1 liter of the supernatant was added 474 g of ammonium sulfate, and the mixture was left standing at 4° C. and then centrifuged to remove the precipitate. To 1 liter of this supernatant was further added 153 g of ammonium sulfate, and the mixture was left standing at 4° C. and then centrifuged to recover the precipitate. The precipitate was dissolved in a solution of 50 mM Tris-HCl (pH 7.0) and 100 mM NaCl, and the solution was passed through a Sep-pak cartridge (a mini-column for adsorption chromatography) (Waters Co.) to adsorb proteins on it. The cartridge was washed with the buffer, and proteins were eluted with 40% acetonitrile and lyophilized. As the protein sample still contained considerable amounts of the culture medium components, it was subjected to gel filtration with Bio-Gel p60 (a polyacrylamide gel) (Biorad Co.) packed column to collect the fraction containing BBRP42, which was dialyzed against 0.1M ammonium hydrogen carbonate and lyophilized to give a sample for the determination of the amino acid sequence.

(2) Determination of amino acid sequence

A 40 μg portion of the protein obtained in the above-mentioned paragraph (1) was subjected to amino acid analysis by an amino acid analyzer 477A (Applied Biosystem Inc.) to analyze 20 amino acid residues from the N-terminus. As a result, the amino acid sequence at positions 4 to 20 from the N-terminus was revealed as follows. (Seq ID No 2):

Ala—Lys—Pro—Thr—Ser—Leu—Asn—Lys—Pro—

Val—Glu—Val—Lys—Phe—Lys—Thr—Gly.

Example 3

Cloning of gene coding for BBRP42 and determination of DNA sequence (1) Construction of a gene library of *Bacillus brevis* 47

The cells obtained by centrifugation in Example 1 were suspended in a solution of 50 mM Tris-HCl (pH 8.0), 50 mM EDTA and 15% sucrose. Lysozyme was added to the suspension so that it had a final concentration of 5 mg/ml, and the mixture was incubated at 37° C. for 15 minutes. Next, SDS and Pronase K were added so that they had final concentrations of 0.5% and 50 μg/ml, respectively, and the mixture was incubated overnight at 55° C. After repeated extractions with phenol and a final extraction with chloroform, ethanol in an amount of 2 times of the mixture was added to precipitate DNA. The DNA was partially digested with Sau3A1 according to the method of Maniatis et al. (Molecular cloning 1982, Cold Spring Harbor Laboratory) and then subjected to agarose gel electrophoresis. A gel containing a DNA fragment of ca. 20 kb was cut out and charged into a dialysis tube, and the DNA was eluted from the gel by electrophoresis. The solution was subjected to extraction with phenol, and the DNA was precipitated with ethanol. The chromosomal DNA (1 μg) and λgt10 DNA (Stratagene Co.) cleaved with BamHI (2 μg) were precipitated with ethanol, dissolved in 10 μl of a ligation buffer [66 mM Tris-Hcl (pH 7.6), 6.6 mM MgCl$_2$, 10 mM DTT, 0.1 mM ATP] and incubated overnight at 16° C. after addition of T4 ligase. A 5 μl portion of the incubation was subjected to packaging with a λDNA in vitro packaging kit and a Gigapack gold (an in vitro phage packaging kit) (Stratagene Co.).

(2) Screening of recombinant phage carrying gene coding for BBRP42

About 5,000 phages obtained in the above-mentioned paragraph (1) were spread on an agar medium with a cell culture of *E. coli* C600 strain and plaque hybridization was carried out according to the method of Maniatis et al. (Molecular cloning 1982, Cold Spring Harbor Laboratory). A probe used was a DNA of 50 nucleotides comprising (Seq ID No 6):

GCTAAACCAACTTCTCTGAACAAACCAGTTGAAGTTAAATTCAAAACTGG, labeled with [γ$^{32}$P] ATP and T4 polynucleotide kinase. The DNA was synthesized on the basis of DNA sequence expected from the amino acid sequence of the positions 4 to 20 obtained in Example 2 and in due consideration of the codon used frequently in the genes coding for the proteins MWP and OWP derived from *Bacillus brevis* 47 which had already been cloned (Tsuboi et al. (1988) J. Bacteriol., 170, 935). As a result, 15 clones which hybridized with the probe were obtained.

(3) Determination of DNA sequence of gene coding for BBRP42

The phage DNA obtained in the above-mentioned paragraph (2) was cleaved with EcoRI and the resultant fragments were subjected to Southern blot hybridization. As a result, the above-mentioned probe hybridized with a fragment of 6.6 kb. An EcoRI fragment of one clone was inserted at an EcoRI site of pUC18 (Takara Shuzo K. K.) to prepare a DNA and a restriction map was prepared. The DNA was cleaved with various restriction enzymes and then subjected to Southern hybridization with the aforementioned probe; a SacI-PstI fragment of 1.7 kb hybridized with the probe. A SalI-SphI fragment of 3.7 kb containing this region was inserted between a SalI site and a SphI site of pHSG399 (Takara Shuzo K. K.). The resultant plasmid DNA was cleaved with SalI and KpnI and then deletion mutants were constructed by stepwise digestion of the DNA with exonuclease III and mungbean nuclease (Heinkoff, (1984), Gene, 28, 351-). DNAs of individual deletion mutants were isolated and DNA sequences were determined using a 7-deaza Sequenase kit (United States Biochemical Corporation). FIGS. 3A-3B shows the DNA sequence from EcoRI site to a HindIII site of pBRE-1, which is one of the deletion mutants. As shown in FIGS. 3A-3B, when the data for the DNA sequence were analyzed, the open reading frame consisting of 457 codons was found in the region from the base pairs No. 237 to No. 1607. The amino acid sequence consisting of 17 amino acids obtained in Example 2 was found in the amino acid sequence between amino acid No. 32 and No. 48 which was translated from this open reading frame. BBRP42 found in the medium had terminus at the N-terminal end of alanine of amino acid No. 29 and the sequence between this position and the N-terminal end is considered to function as a secretion signal. There are six sites which potentially make the translation initiating points, Met, from amino acid No. 1 to No. 28. The structure in which Met at position 1 is a translation initiating point is very similar to the one common to the secretion signal of genus Bacillus already investigated, consisting of hydrophilic site—hydrophobic site—cleavage sites, in this order form the N-terminal end.

(4) Determination of transcription initiating point of the gene coding for BBRP42, a DNA consisting of 20 nucleotides complementary to the sequence from base pairs No. 225 to No. 244 shown in FIGS. 3A-3B was synthesized, and then primer extension was carried out (Jones, K. A., (1985) Cell 42, 559-572). The RNA of Bacillus brevis 47 isolated according to the method of M. Z. Gilman et al. (Cell, 35, 285-293) and the above-mentioned primer labeled with [$\gamma^{32}P$] ATP and T4 polynucleotide kinase were annealed, and a complementary strand was synthesized with a reverse transcriptase. The product was subjected to electrophoresis together with size markers on a 7M urea/10% acrylamide gel to determine the length of the strand. As a results of autoradiography, bands of 60 nucleotides and No. 61 nucleotides were confirmed, and thus the transcription initiating point of the gene coding for BBRP42 was concluded to be G at the nucleotide position 185 and T at the nucleotide position 184 shown in FIGS. 3A-3B. G at the position 185 is major and T at the position 184 is minor.

Example 4

Construction of expression unit vector

Plasmid pBRE-1 carrying the DNA fragment shown in FIG. 3 which was selected from the deletion mutants obtained in Example 3 was cleaved with EcoRI and PstI to give a DNA fragment containing a promoter, a signal peptide and the N-terminal region of BBRP42. The DNA fragment was inserted between an EcoRI site and a PstI site of a plasmid vector, pUC18, to construct pBRE-2. A DNA sequence between a BsmI site and a PstI site of this pBRE-2 was replaced by synthetic complementary DNAs having the following DNA sequences to construct pBRE-3/(Seq ID No 7):

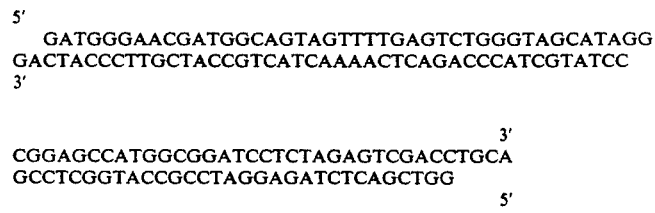

The plasmid thus constructed has the promoter of the gene coding for BBRP42, encodes the signal peptide of BBRP42, and furthermore carries downstream a polycloning site comprising NcoI, BamHI, XbaI, PstI, SphI, and HindIII sites. By ligating a heterologous protein gene directly to the NcoI site, one expression unit can be constructed. In ligating the gene, it is necessary to add a DNA coding for Ala at the 5' end since the DNA site coding for Ala, the last amino acid of the signal peptide, is cleaved by the digestion with NcoI. Furthermore, as the plasmid is not replicable in Bacillus brevis, it is necessary to transfer the expression unit constructed on pBRE-3 to a plasmid which is replicable in Bacillus brevis 47. For example, it is necessary to insert a DNA fragment, which is obtained by cleavage with EcoRI and HindIII of a plasmid in which a heterologous protein gene is incorporated in pBRE-3, into an appropriate site of a shuttle vector such as pHP13 which is replicable in the cells of Bacillus strains.

Typical expressions of α-amylase of B. licheniformis and human epidermal growth factor are illustrated in the following.

Example 5

Construction of the expression vector of αamylase of B. licheniformis and its expression in Bacillus brevis 47

The DNA fragment cleaved with BamHI and BclII from a plasmid pTN1 containing the α-amylase gene of B. licheniformis (T. Yuuki, et al., (1985), J. Biochem., 98, 147-) was inserted into the BamHI site of the pBRE-3 prepared in Example 4, and the product in which the amylase gene was arranged in the correct direction was selected to prepare pAMY-1. A waste portion was deleted from the plasmid with NcoI and Ceo47III, and a pair of synthetic DNAs represented by the following structure was inserted in lieu of the waste portion to prepare pAMY-2:

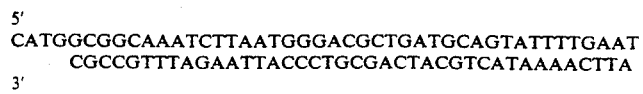

```
                                    3'
GGTACATGCCCAATGACGGCCAACATTGGAAGC
CCATGTACGGGTTACTGCCGGTTGTAACCTTCG
                                    5'
```

The pAMY-2 (Seq ID No: 8) contains a promoter of a gene coding for BBRP42, and an expression unit coding for a signal peptide of BBRP42 as well as α-amylase of B. licheniformis. Furthermore, pAMY-3 was prepared by cleaving a DNA containing an expression unit from pAMY-2 with EcoRI and HindIII and inserting it into an EcoRI and HindIII site of pHP13 which is one of the shuttle vectors of E. coli and B. subtilis. Bacillus brevis 47 was transformed with the plasmid thus prepared according to the method of Takahashi et al. (J. Bacteriol., (1983), 156, 1130-1134). The resultant transformant was inoculated on a T2 culture medium (1% peptone, 0.5% meat extract, 0.2% yeast extract, 1% glucose) containing 10 μg/ml of erythromycin, and shaking culture was carried out at 37° C. The cells were removed from the culture medium by centrifugation, and the activity of amylase in the supernatant was determined by the Matsuzaki's modification of the method of H. Fuwa (J. Biochemistry, 41, 583, 1954). As a result, it was confirmed that amylase was secreted into the culture medium.

Example 6

Quantitative determination of amylase secreted by Bacillus brevis 47 transformed by pAMY-3

Figure 7:
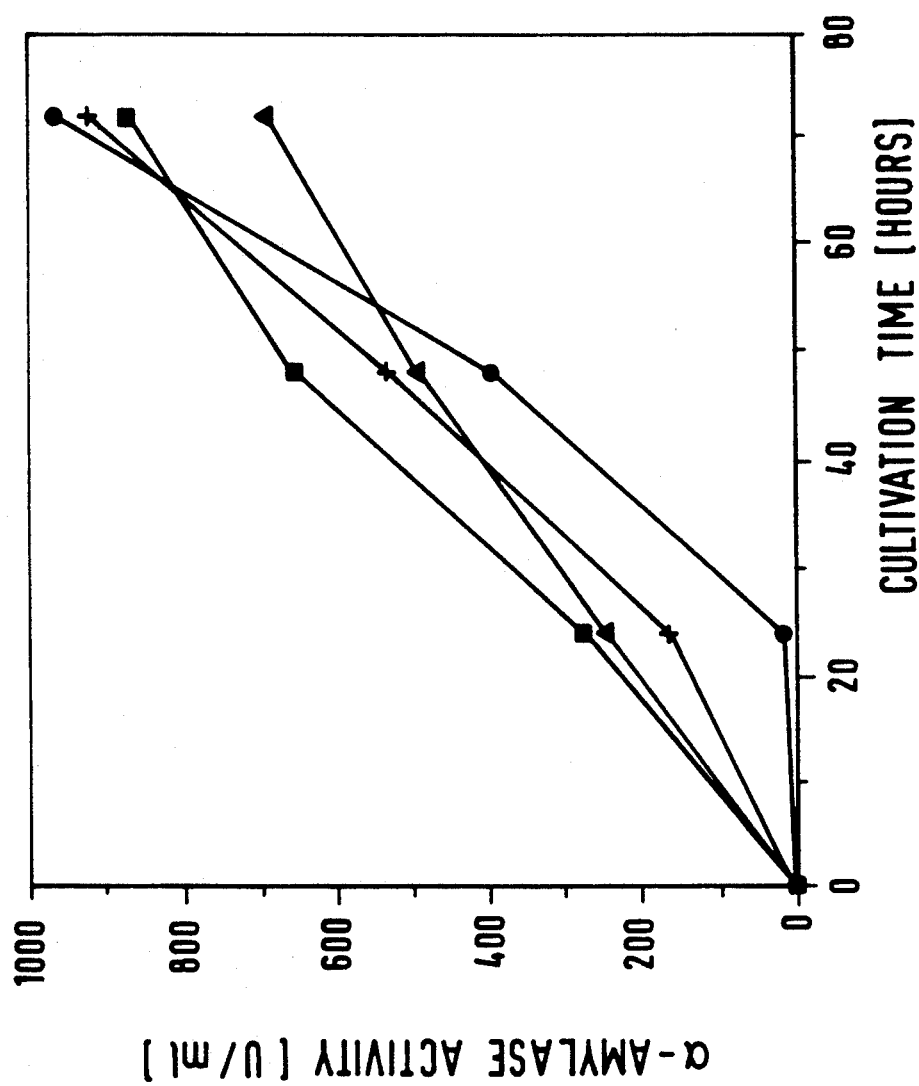
FIG. 7 is a graph which illustrates the change of the activity of α-amylase secreted by *Bacillus brevis* 47 transformed by pAMY-3 with the passage of culture time, in which—●—and -▲-represent the amylase activities in a T2 culture medium containing 10 and 200 µg/ml of erythromycin, respectively, -■-represents the amylase activity in the LS culture medium containing 200 µg/ml of erythromycin and —+— represents the amylase activity in the LS culture medium containing 200 μg/ml of erythromycin and 1% of glucose.

The transformant of Bacillus brevis 47 containing pAMY-3 obtained in Example 5 was inoculated in the T2 medium containing 10 μg/ml of erythromycin, the T2 medium containing 200 μg/ml of erythromycin, the LS medium (1% peptone, 0.5% yeast extract, 0.25% sodium chloride) containing 200 μg/ml of erythromycin, or the LS medium containing 1% glucose and 200 μg/ml of erythromycin, and shaking culture was carried out at 37° C. A portion of the culture medium was taken out at every 24 hours, and the supernatant in which the cells had been removed by centrifugation was used as an amylase sample solution for the determination of its activity. The amylase activity in the supernatant was determined by the Matsuzaki's modification of the method of H. Fuwa as in Example 5. FIG. 7 shows the amylase activities secreted into the supernatant with the passage of time. After culture for 24 hours, amylase was secreted in the largest amount in the LS medium containing 200 μg/ml of erythromycin, and the secretion of amylase was decreased sequentially in the T2 medium containing 200 μg/ml of erythromycin, the LS medium containing 1% glucose and 200 μg/ml of erythromycin and the T2 medium containing 10 μg/ml of erythromycin. However, after culture for 72 hours, the amylase activity was decreased in the sequence of those in the LS medium containing 1% glucose and 200 μg/ml of erythromycin, the LS medium containing 200 μg/ml of erythromycin and the T2 medium containing 200 μg/ml of erythromycin. In the T2 medium containing 10 μg/ml of erythromycin after culture for 72 hours, 920 U/ml of amylase was secreted.

Example 7

Construction of expression vector of human epidermal growth factor (h-EGF) and expression in Bacillus brevis 47

Human epidermal growth factor is a comparatively small polypeptide comprising 58 amino acids, and a chemically synthesized DNA was used in this experiment as a DNA coding for the human epidermal growth factor. In the synthesis of the DNA, a DNA comprising a sequence coding for Ala which is the last amino acid of the signal sequence in the upstream, a TAA coding for a terminating codon in the downstream and the DNAs capable of linking to NcoI and XbaI sites at both terminals were synthesized in four portions. The synthetic DNA was inserted into the NcoI and XbaI sites of pBRE-3 to prepare pEGF-1. The DNA fragment cleaved from the plasmid with EcoRI and HindIII was inserted into pHP13 to prepare pEGF-2. The expression vector was introduced into Bacillus brevis 47 in the same manner as in Example 5. The resultant transformant was inoculated on the T2 medium containing 10 μg/ml of erythromycin, and shaking culture was conducted at 37° C. As a result of the detection of h-EGF in the supernatant, from which the cells had been removed, with anti h-EGF antibody, h-EGF was confirmed in the supernatant.

Example 8

Quantitative determination of h-EGF secreted by Bacillus brevis 47 transformed by pEGF-2

Figure 8:
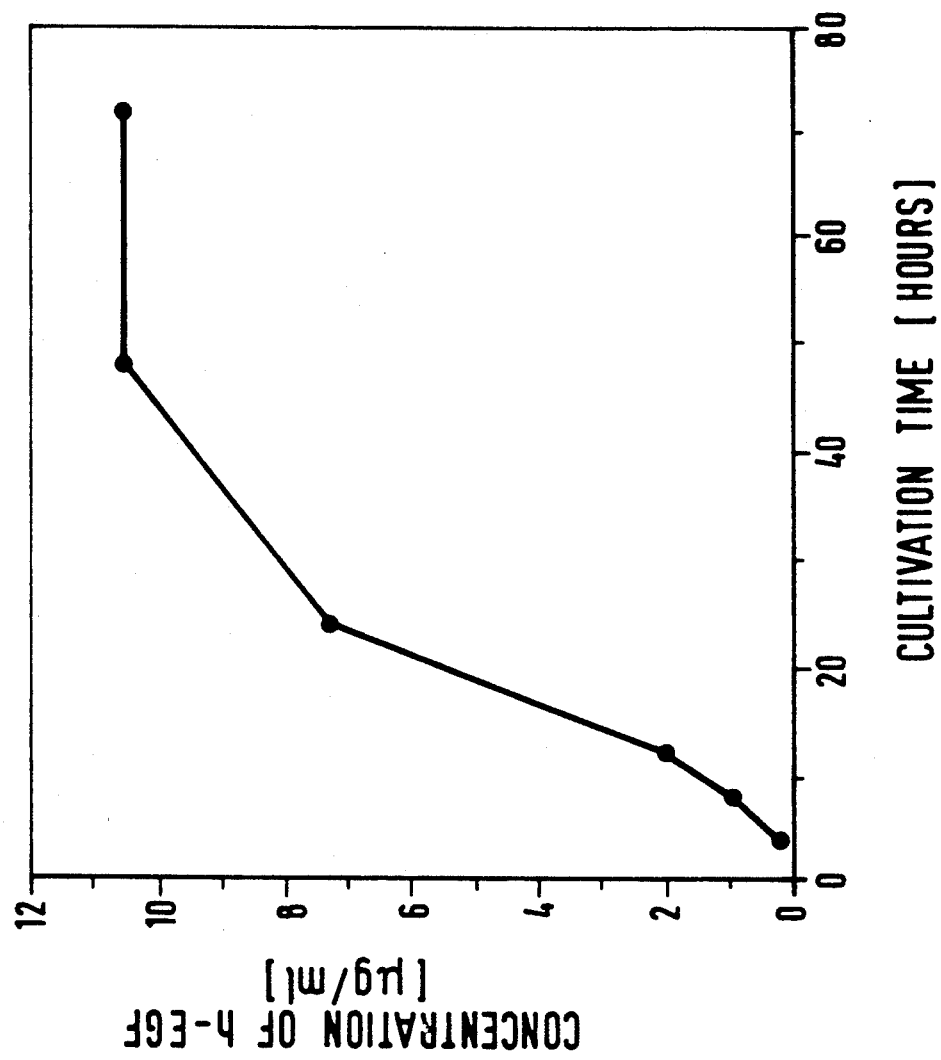
FIG. 8 is a graph which illustrates the change of h-EGF secreted by *Bacillus brevis* 47 transformed by pEGF-2 with the passage of culture time.

Bacillus brevis 47 transformed by pEGF-2 obtained in Example 7 was inoculated in the T2 medium containing 10 μg/ml of erythromycin, and shaking culture was carried out at 37° C. A portion of the culture medium was taken out at every 24 hours, and the concentration of h-EGF in the supernatant from which the cells had been removed was determined by the ELISA method with a monoclonal antibody to the human epidermal growth factor (Current protocols in molecular biology, Vol. 2; Green Publishing Associates and Wiley-Interscience, 1989). As the standard sample, a purified recombinant human EGF (Ars Seiyaku K. K.) was used. FIG. 8 shows the result thereof. While the amount of h-EGF was increased for 48 hours of cultivation, no increase in the amount was observed even in further cultivation. The concentration of h-EGF after cultivation for 48 hours was 10.5 μg/ml.

Example 9

Purification of h-EGF secreted by Bacillus brevis 47 and confirmation of amino acid sequence at N-terminus In order to confirm that the signal peptide at the N-terminus of h-EGF secreted from Bacillus brevis 47 had been cleaved correctly, the h-EGF was purified. Bacillus brevis 47 transformed by pEGF-2 obtained in Example 7 was inoculated in the LS medium containing 10 μg/ml of erythromycin, and shaking culture was carried out at 37° C. for 48 hours. To 40 ml of the supernatant of the culture medium was added 9.72 g of ammonium sulfate, and the mixture was left standing at 4°

C. for 1 hour. The residue was removed by centrifugation, and the supernatant was adsorbed onto a column with which BUTYL-TOYOPEARL 650S (Toso K. K., Japan) had been packed. After the column was washed with PBS (0.8% Nacl, 0.02% KCl, 0.144% Na2HPO4, 0.024% KH2PO4, pH 7.4) containing 40% ammonium sulfate, the concentration of ammonium sulfate was gradually decreased from 40% to 0% to elute h-EGF. In order to further purify the h-EGF containing fraction among the eluates by high performance liquid chromatography, the fraction was adsorbed on a C18 column (packed column for HIGHBAR high performance liquid chromatography, LiChrospher 100 RP-18; Kanto Kagaku K. K., Japan), and h-EGF was eluted with gradient from 0% to 40% of an acetonitrile solution containing 0.1% trifluoroacetic acid. The fractions containing h-EGF were collected, and a portion of the collection was used for the determination of the sequence of 20 amino acids at the N-terminus (ABI Co.; 477A). The amino acid sequence obtained (Seq ID NO: 9) is represented as follows:

Asn—Ser—Asp—Ser—Glu—X—Pro—Leu—Ser—His—Asp—

Gly—Tyr—X—Leu—His—Asp—Gly—Val—X, wherein X represents any residues which cannot be read. The amino acid residue at the N-terminal end was Asn, which was in accord with the residue at the N-terminal end of human epidermal growth factor, and it was confirmed that the signal sequence was cleaved correctly. The residue which cannot be read indicate that the amino acid cannot be analyzed because of its modification or that the amino acid is a Cys residue. All of the amino acid residues of the human epidermal growth factor corresponding to the residue X in the amino acid sequence obtained in this experiment are Cys residues, and X corresponds to Cys. Thus, it is concluded that 20 amino acids at the N-terminus of h-EGF secreted from *Bacillus brevis* 47 have the correct sequence.

Example 10

Secretion and expression of proinsulin derivative inherent in monkey by *Bacillus brevis* 47

Examination was carried out for the secretion and expression of a proinsulin derivative inherent in a monkey in *Bacillus brevis* 47 was carried out. FIG. 9 shows a gene used in the examination.

Figure 10:
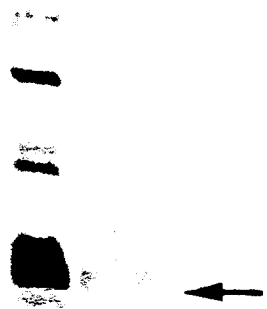
FIG. 10 shows the results of the analysis by Western Blotting of the protein secreted from *Bacillus brevis* 47 transformed by pINT90d2, in which lane 1 and 2 corresponds to a monkey proinsulin derivative of expressed in *E. coli* and *Bacillus brevis* 47, respectively, and the arrow indicates the proinsulin derivative.

The derivative has additionally an artificial amino acid sequence represented as follows at the N-terminus of the proinsulin of a monkey: Met-Ala-Thr-Thr-Ser-Thr-Gly-Asn-Ser-Ala-Arg (Seq ID No: 10). The DNA fragment coding for the derivative was inserted between the NcoI site and SalI site of the expression vector pBRE-3 obtained in Example 4 to prepare pINT90D1. An expression unit cleaved from the plasmid with EcoRI and HindIII was inserted between the EcoRI site and the HindIII site of pHP13 to prepare pINT90D2. pINT90d2 was introduced into *Bacillus brevis* 47. The resultant transformant was inoculated into the T2 medium containing 200 μg/ml of erythromycin, and shaking culture was conducted at 37° C. for 48 hours. An 1 ml portion of the culture medium was centrifuged to remove the cells. The supernatant was lyophilized, and proteins were separated by SDS-polyacrylamide electrophoresis according to the method of Laemmli (describe above). The proteins were transferred electrophoretically on a nylon membrane, and Western-Blotting was carried out with an anti-human-insulin antibody and a secondary antibody labeled with horse radish peroxidase (Current protocols in molecular biology, Vol. 2; Green Publishing Associates and Wiley-Interscience, 1989). As a result, a single protein reactive with the anti-human-insulin antibody was confirmed as shown in FIG. 10.

---

We claim:

1. Isolated and purified DNA encoding a fusion protein comprising a first DNA sequence, which encodes a signal peptide, and a second DNA sequence, which encodes a gene of interest operably linked to the first DNA sequence, wherein the amino acid sequence of the signal peptide is (I) (SEQ ID No 1): Met-Phe-Ser-Lys-Thr-Lys-Met-Gly-Met-Leu-Met-Gly-Thr-Met-Ala-Val-Val-Leu-Ser-Leu-Gly-Ser-Ile-Gly-Gly-Ala-Met-Ala.

2. Isolated and purified DNA as claimed in claim 1, wherein the first DNA sequence is (II) (SEQ ID NO 3): ATG-TTT-AGC-AAA-ACA-AAA-ATG-GGA-ATG-CTG-ATG-GGA-ACG-ATG-GCA-GTA-GTT-TTG-AGT-CTG-GGT-AGC-ATA-GGC-GGA-GCM-ATG-GCR; wherein M represents A or C, and R represents A or G.

3. An expression vector comprising the isolated and purified DNA as claimed in claim 1, and additional DNA required for expression of the fusion protein comprising a promoter, a transcription starting point, and a translation starting point.

4. The expression vector as claimed in claim 3, wherein the DNA sequence of the promoter is (III) (SEQ ID NO 4): TACGA TTTTC CCTCA AGTTT TCCTT TTTTC TCAAA CGGGA ATCTA AAAAT ACCCA TGTAC ACTTG GTCTT.

5. The expression vector as claimed in claim 3, wherein said vector further comprises a translation regulating signal between the transcription starting point and the translation starting point.

6. The expression vector as claimed in claim 5 wherein the DNA sequence of the translation regulating signal is (IV) (SEQ ID NO 5): GTAAC AAAGA ACAAG CACAC TACAC GAGCA TAGAC GAAAG GGTTG AGTGT AT.

7. A process for preparing a desired protein, which comprises transforming a host cell with the vector according to claim 3 and culturing the transformant prepared so that said desired protein will be secreted into a culture medium.

8. The process according to claim 7, wherein said host cell is a strain of genus Bacillus.

9. The process according to claim 8, wherein said strain of genus Bacillus is *Bacillus brevis*.

* * * * *